(12) United States Patent
Ruetenik

(10) Patent No.: US 10,292,872 B2
(45) Date of Patent: May 21, 2019

(54) EQUINE LEG CAST ROCKER ATTACHMENT

(71) Applicant: Monty L. Ruetenik, Clear Lake Shores, TX (US)

(72) Inventor: Monty L. Ruetenik, Clear Lake Shores, TX (US)

(*) Notice: Subject to any disclaimer, the term of this patent is extended or adjusted under 35 U.S.C. 154(b) by 482 days.

(21) Appl. No.: 15/149,102

(22) Filed: May 7, 2016

(65) Prior Publication Data

US 2016/0250078 A1    Sep. 1, 2016

Related U.S. Application Data

(63) Continuation-in-part of application No. 14/046,751, filed on Oct. 4, 2013, now abandoned.

(51) Int. Cl.
| | | |
|---|---|---|
| *A61D 9/00* | (2006.01) | |
| *A01K 13/00* | (2006.01) | |
| *A61F 13/04* | (2006.01) | |
| *A61F 15/00* | (2006.01) | |
| *A61F 5/058* | (2006.01) | |

(52) U.S. Cl.
CPC .......... *A61F 13/043* (2013.01); *A01K 13/007* (2013.01); *A61D 9/00* (2013.01); *A61F 5/0585* (2013.01); *A61F 15/004* (2013.01)

(58) Field of Classification Search
CPC ................................................... A61F 5/0585
See application file for complete search history.

(56) References Cited

U.S. PATENT DOCUMENTS

| | | | | |
|---|---|---|---|---|
| 1,337,194 | A * | 4/1920 | Capewell | A01L 3/04 168/21 |
| 1,383,508 | A * | 7/1921 | Mitro | A01L 3/02 168/1 |
| 4,237,981 | A * | 12/1980 | Stubbe | A01L 3/00 168/4 |
| 6,868,656 | B2 * | 3/2005 | Osha | A01K 13/007 168/2 |
| 2009/0032270 | A1 * | 2/2009 | Ruetenik | A01K 13/007 168/28 |
| 2010/0031614 | A1 * | 2/2010 | Osborne | A01K 13/007 54/82 |

FOREIGN PATENT DOCUMENTS

GB    2519061 A  *  4/2015   ........... A01K 13/007

* cited by examiner

*Primary Examiner* — Tarla R Patel
(74) *Attorney, Agent, or Firm* — Douglas Baldwin

(57) ABSTRACT

A device or structure for fitting on the bottom of an equine leg cast to protect the cast from abrasion and wear, to aid in keeping the cast clean and, in one aspect, to provide a shaped molded rocker bottom that allows the leg cast hoof to rock forward or back, allowing the equine to find a naturally comfortable position. A method of applying the device to an equine leg cast. The device or structure consist, in general, of a solid member having a top face and a bottom face and having malleable straps attached to the solid member and extending from at least two sides of the solid member, which straps are made of material and sized to be capable of being bent or folded upward in a plane perpendicular to the top face of the solid member to attach to an equine leg cast.

20 Claims, 5 Drawing Sheets

US 10,292,872 B2

EQUINE LEG CAST ROCKER ATTACHMENT

CROSS-REFERENCE TO RELATED APPLICATION

This application is a continuation-in-part of application Ser. No. 14/046,751, filed Oct. 4, 2013 and claims the benefit and priority from U.S. Provisional Patent Application 61/881,556 filed Sep. 24, 2013, the contents and disclosure of both are incorporated herein by reference for all purposes.

FIELD OF THE INVENTION

A device for fitting on the bottom of an equine leg cast to protect the cast from abrasion and wear, to aid in keeping the cast clean and, in one aspect, to provide a shaped molded rocker bottom that allows the leg cast hoof to rock forward or back, allowing the equine to find a naturally comfortable position.

BACKGROUND

Equine leg casts are used for a variety of problems such as certain bone fractures, tendon and ligament injuries, wounds, and abnormal growth and development. Increasingly, veterinarians are also casting the hoofs of laminitic horses to stabilize the hoof in order to prevent further injury. Casts are often useful as first aid tools, for immobilization of limbs, to overcome tension which helps keep skin from pulling apart at wound sites, as rigid support to allow a horse to stand and use a limb during convalescence, and for protection and reduced concussion to a limb. Casts also provide external support and reinforcement for internal fixation devices such as plates or screws used in fracture repair.

One of the more serious difficulties with a typical cast is the lack of protection on the bottom of the cast so that the fiberglass or other cast material is abraded during use and the bottom becomes soiled and otherwise damaged. Another problem is that often the casting procedure fixes the leg in an awkward position. For example, when casting horses that are lying down, the hoof may inadvertently be set in a position that is unnatural for the equine. When casting, the leg is unloaded and non-weight-bearing so there is no tension on ligaments and tendons.

It is currently customary for some practitioners to use a non-ergonomically shaped wad of casting material at the base of the cast to provide a "rocker" effect. But in so doing there is no consistency and no repeatability from cast to cast. It is important to establish better standards of care so that more practitioners can perform the same procedure without need of an expensive specialist.

The present invention provides a high degree of consistency so that the level of care provided to the equine can be made without the services of an expensive podiatrist or specialist or outsourcing the patient to a referral clinic. The cast attachment of this invention is cost effective and provides consistency and repeatability. The equine leg cast attachment rocker helps to protect and stabilize the leg cast and provides more secure and natural footing for equines with a leg cast. The rocker bottom on the equine attachment allows the equine to find a comfortable position by allowing rotation or enabling a reduction of torque on the hoof.

DESCRIPTION OF THE DRAWINGS

The accompanying drawings, which are incorporated into and constitute a part of the Specification, illustrate specific embodiments of the invention and, together with the general description of the invention given above, and the detailed description of the specific embodiments, serve to explain the principles of the invention.

SUMMARY

In broad scope the invention is attachment for an equine leg cast that is a solid whole member (structure) having a top face and a bottom face and having malleable straps attached to it that extend from at least two sides. The malleable straps are made of material and sized to be capable of being bent or folded upward in a plane perpendicular to the top face of the solid whole member to attach to the sides of an equine leg cast. Suitable strap widths are between about 3 to 16 percent of the length of the circumference of the solid whole member measured at the top side of the solid member. It is also a method of applying and using the attachment.

DETAILED DESCRIPTION

In broad aspect this invention is an attachment and method for improving casted equine mobility and for protection of the bottom of equine leg casts. More specifically, it is, in one aspect, an equine leg cast bottom attachment comprising a solid whole member having a top and a bottom and having malleable (metal or fabric) straps that may be contoured to the sided of a leg cast and extending from at least two sides of the of the solid member. The straps may be bent or folded upward in a plane perpendicular to the top face of the solid member to attach to an equine leg cast.

Figure 1:
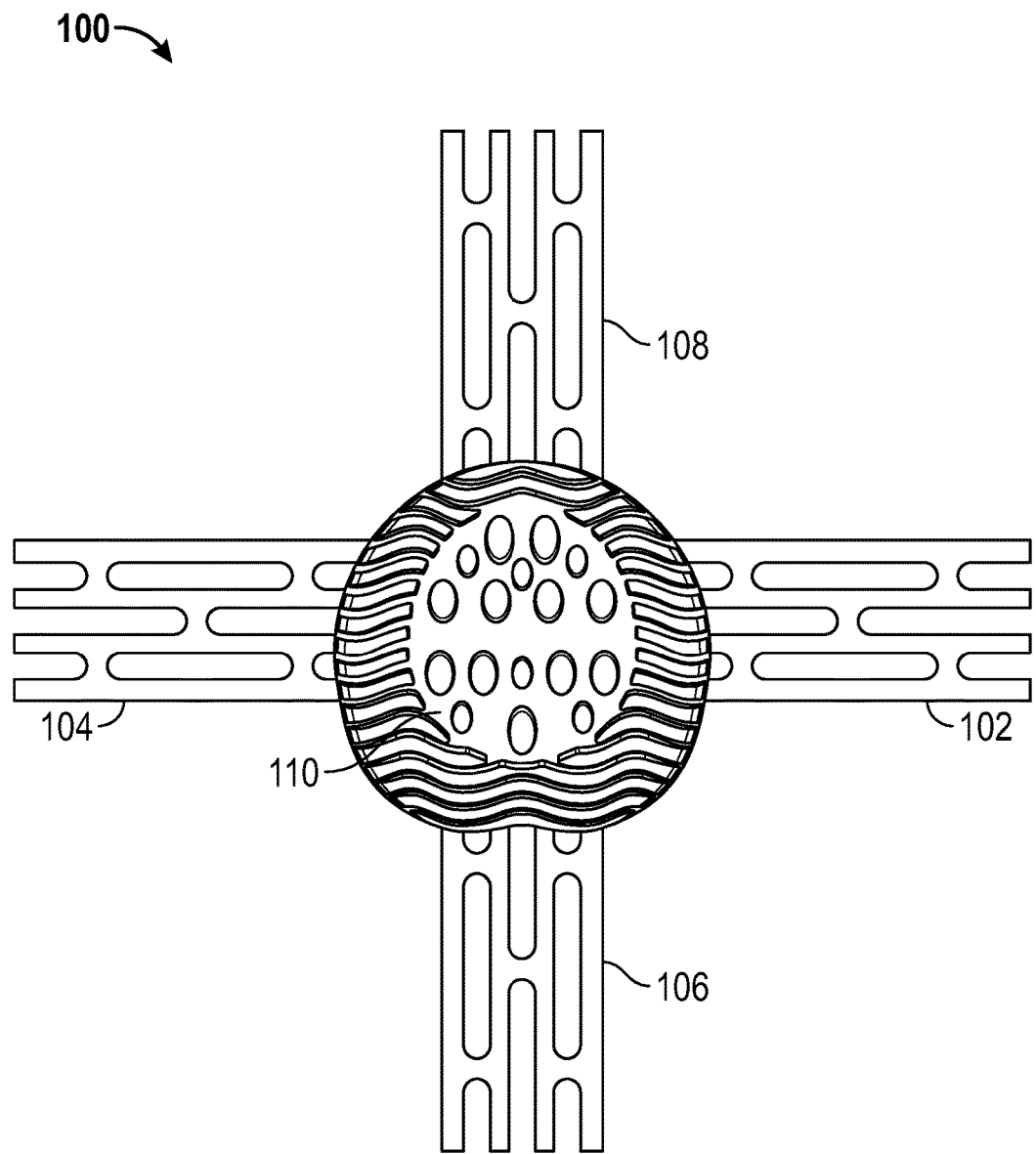
FIG. 1 is a bottom view of an embodiment of the invention showing the solid member with perforated metal straps.

Referring to the Figures, FIG. 1 shows a bottom view of an embodiment, 100, of the invention. As shown in FIG. 1 there is a solid whole member, 110. The solid whole member has a top side and bottom side, the bottom being intended to be in contact with the ground when the attachment is attached to a leg cast. The bottom (110) as shown is patterned to provide more secure footing and stable contact with the ground or surface on which the equine stands. The patterning is not an essential feature of the invention but is preferred. Patterning may be any suitable design including groves, ridges, holes and dots. The solid member may be of any suitable material such as wood, rubber, moldable metal and the like but molded polymer material such as polyurethane is preferred.

The solid whole member is a solid whole structure, as those illustrated in the drawings, having no opening in the center as is the case with a conventional horseshoe. While there may be small openings for attachment to a cast, there is no substantial center opening. The structure is therefore termed "structurally whole" and "solid whole" and the term "structurally whole" and "solid whole" used herein and in the claims means a structure as described above with no substantial central opening. The term "solid member" also means a solid whole member. These structures are also referred to herein as a "rocker". Generally the solid whole member will be made of a single material of construction, that is, it will be constructed of one kind of material such as a single polymer, wood or metal. It may also be made of a polymer with fillers such as particles of a different material or fibers but will not be a combination of different materials joined together. Thus, the term "single material" as used herein in regard to the solid whole member means a structure constructed of a single material of construction as described above and may include polymer materials with fillers.

Metal straps 102, 104, 106 and 108 are attached to the structurally whole solid member as shown. As shown, the straps are fashioned into a molded polymer member about a ¼ inch from the top surface of the solid member. The straps may be attached to the solid member in any number of ways but are preferably attached near the top (in the upper half of the member) as illustrated in the Figures. It is preferred that the solid member be of molded polymer material and in a preferred embodiment molded polyurethane elastomer. It is essential that the straps be sufficiently flexible to be bent or folded upward and contoured into the sided of cast material on an equine leg to a position perpendicular to the plane of the top and bottom of the solid member. The straps on opposite sides of the solid member may be a single piece that extends across or through the solid member and extends out on opposites sides. Thus, if the solid member is molded polymer, straps can be laid in the top portion of the mold, extending out from each side of the mold and the polymer poured into the mold to set, resulting in a solid member with two side straps on opposite sides of the solid member. If the solid member is a completed structure prior to attaching the straps, for example if the solid member is wood or pre-molded polymer, the straps may be attached by any suitable conventional means, such as with screws, nails, adhesive or insertion through a slot in the solid member and similar means.

Figure 5:
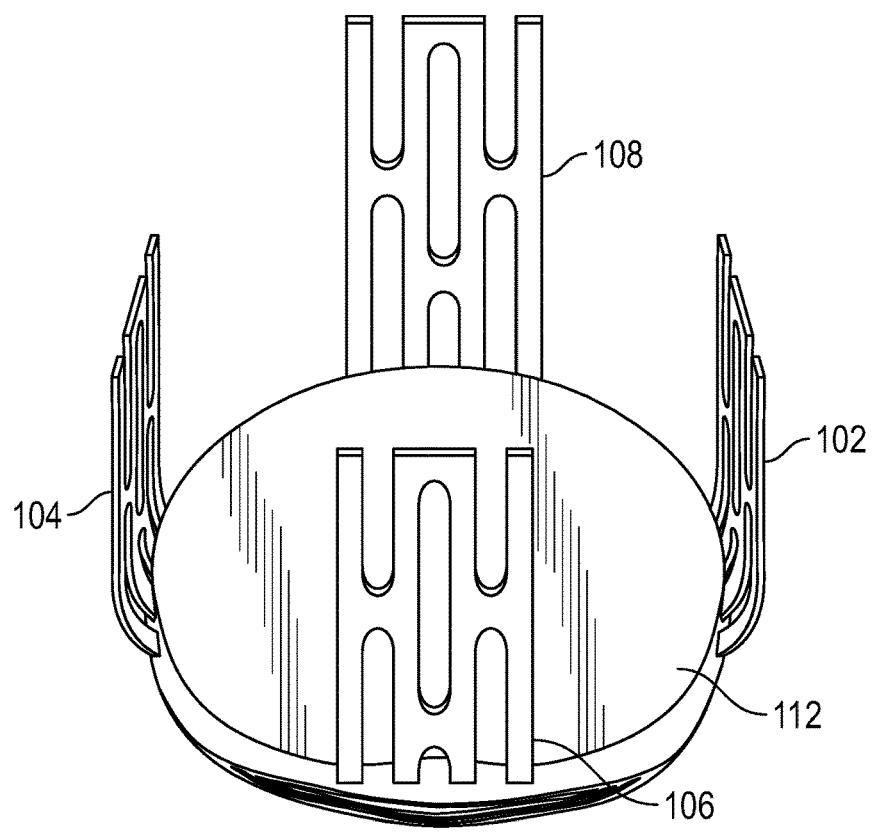
FIG. 5 is a top perspective view of an embodiment of the invention with metal strap bent upward in position to attach to an equine leg cast.
Figure 6:
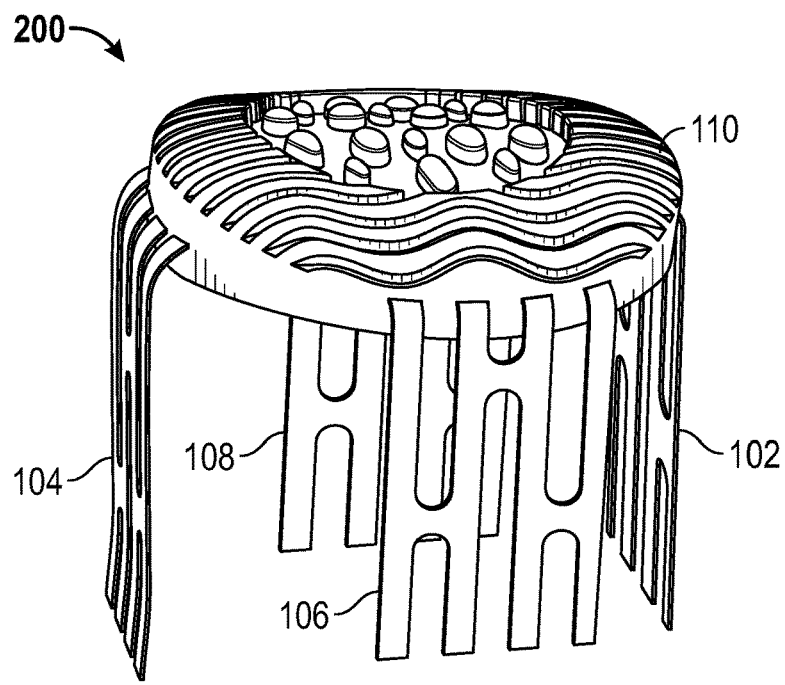
FIG. 6 is a bottom perspective view of an embodiment of the invention with four metal straps bent upward in position to attach to an equine leg cast.
Figure 7:
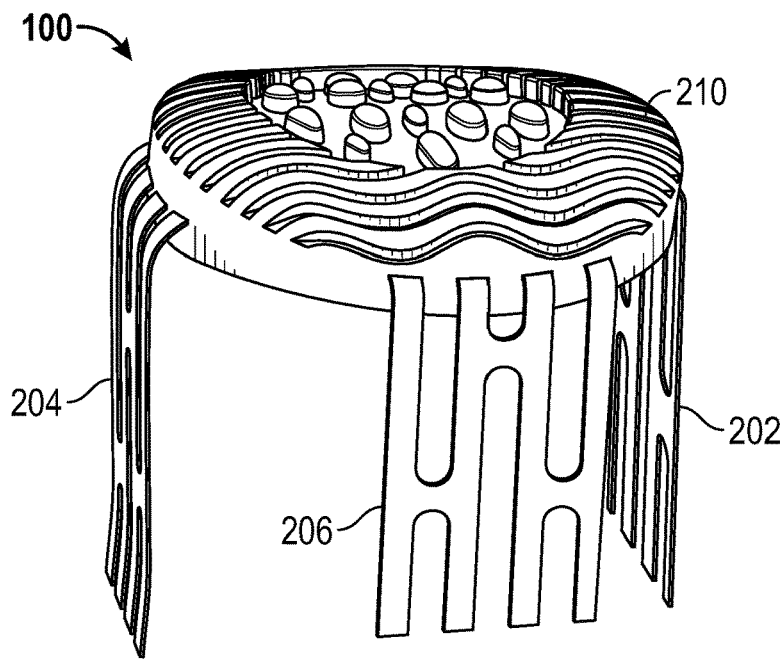
FIG. 7 is a bottom perspective view of an embodiment of the invention with three metal straps bent upward in position to attach to an equine leg cast.
Figure 8:
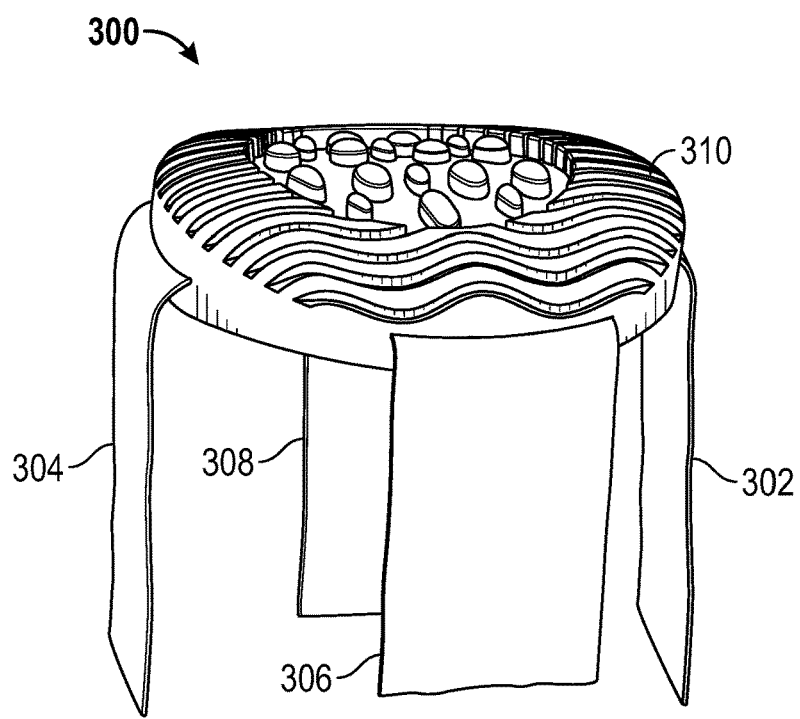
FIG. 8 is a bottom perspective view of an embodiment of the invention with four fabric straps folded upward in position to attach to an equine leg cast.
Figure 9:
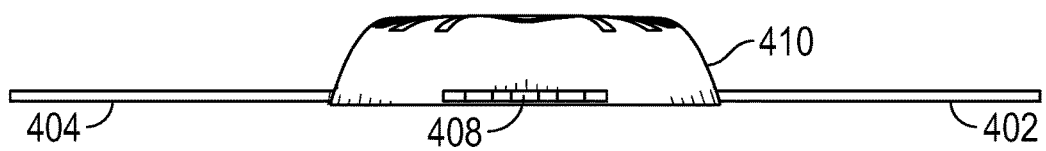
FIG. 9 is a rear edge view of an embodiment of the invention.
Figure 10:
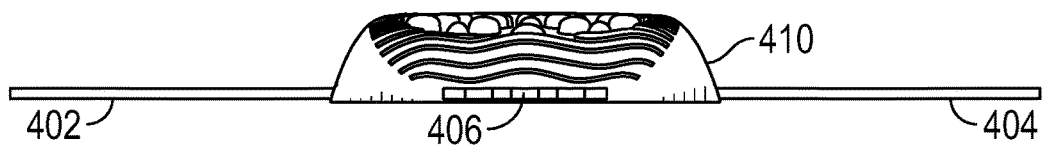
FIG. 10 is a front edge view of an embodiment of the invention.
Figure 11:
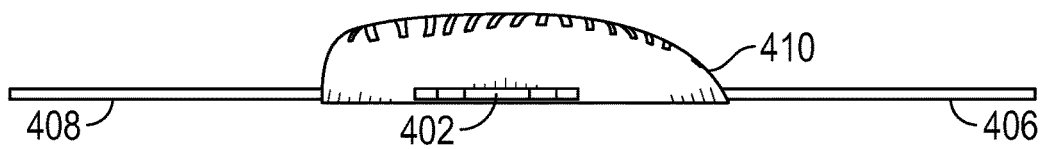
FIG. 11 is a side edge view of an embodiment of the invention.

FIGS. 5, 6, 7 and 8 illustrate the straps folded up and contoured to fit a leg/cast shape FIGS. 6, 7 and 8 show the attachment inverted from normal positioning on an equine leg cast in order to illustrate the patterned bottom. FIG. 5 shows an embodiment as it is positioned in use as on a cast.

Figure 2:
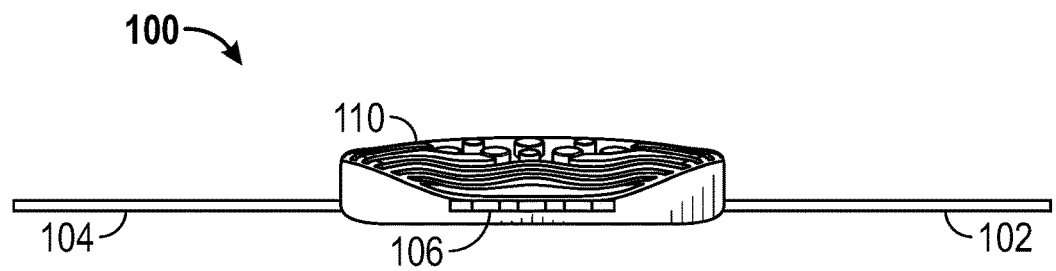
FIG. 2 is a front edge view of an embodiment of the invention.
Figure 3:
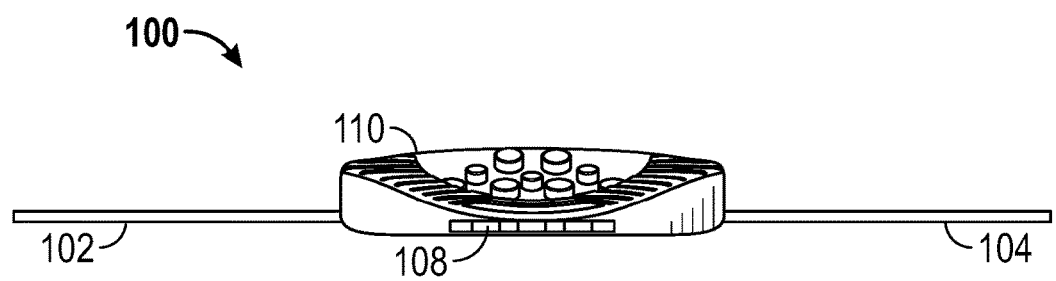
FIG. 3 is a rear edge view of an embodiment of the invention.
Figure 4:
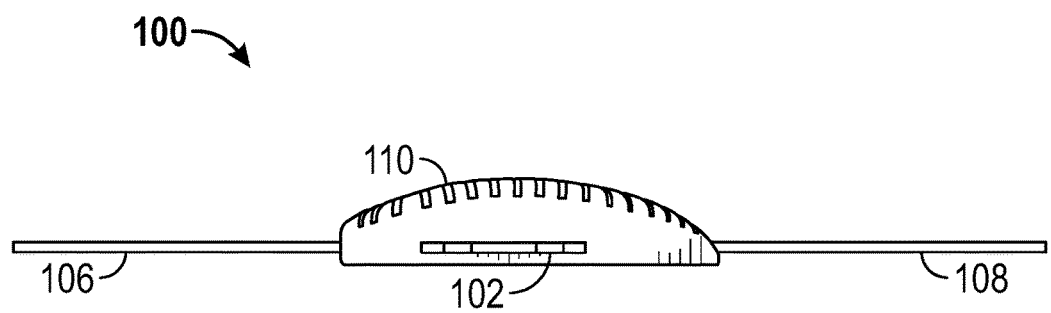
FIG. 4 is a side edge view of an embodiment of the invention.

FIGS. 2, 3, 4, 9, 10, 11 and 12 are side and end views of a solid member that is tapered to form a molded "rocker" configuration. These Figures show the way the solid member may be tapered and the way the straps are molded in near the top side of the member. The tapers of the molded member may be varied to provide the type rocker action desired. The rocker structure illustrated in FIGS. 2, 3 and 4 is sloped to the front and sloped to the rear of the solid member. This allows maximum flexibility of movement and allows the horse more options to find the optimum comfortable position but is least stable of the configurations. This rocker shape is useful to enhance self-stretching of ligaments as when preparing for exercise, much like a person stretching the Achilles tendons by leaning on a wall before a run.

It is also suitable to have the solid whole rocker sloped only to the front, the front will be tapered as shown in the Figures but the rear will be essentially flat from the center to the rear of the member to allow more stable footing as is illustrate in FIGS. 9, 10, 11 and 12. This configuration provides the equine a more stable footing in a preferred neutral resting position. The neutral resting position in the rear section of the device enables the horse to have a stable place to rest, yet if there is movement fore and aft or laterally the solid whole rocker rolls to lessen torque on the tendons, ligaments and especially on compromised lamina. This configuration is generally preferred.

Both styles of rocker configuration (sloped only to the front and sloped front and rear) are useful in appropriate situations and both are within the scope of this invention The narrowed toe of the solid whole rocker enhances lateral break-over and provides the equine with more flexibility of movement.

Various ways in which this solid member may be tapered are within the scope of this invention. A number of possible shapes are described in co-pending US published application No. 2011/0067366, Mar. 24, 2011 (Ser. No. 12/882,352), incorporated herein by reference for all purposes. The tapered shape on the bottom moves the break-over point back as well as helping isolate the lateral forces on the cast and thereby on the bone column.

An advantage of the solid whole rocker attachment is that it greatly reduces the surface area in contact with the ground or other surface onto which the equine stands. For example, a typical cast bottom would be about 8 inches×8 inches or 64 square inches. A suitable rocker attachment will be about 4 inches×5 inches or 20 square inches which is only about 30% of the surface of the cast bottom. Smaller rockers will reduce ground contact even further.

The Figures illustrate straps of expanded or perforated metal molded into the upper portion of the solid whole member. The straps protrude out laterally and in use are folded up to attach to an equine leg cast. The expanded or perforated metal reduces the weight and is more easily molded to contour to the anatomical confirmation of the horse's leg around the cast. It allows a good bond with the casting adhesive and allows practitioners to bend it upward to attach to the casting material.

There may be only three straps extending from the sides of the solid whole member in one aspect of the invention as shown in FIG. 7 but four are preferred. It may also be advantageous to have five (5) straps spaced around the solid member. Five straps will position the straps in a way that will facilitate cutting the cast when it is to be removed. FIG. 1 shows the straps in the same plane as the molded member as would be suitable for packaging and shipping. But in use they are folded up and against the sides of a cast and attached to the cast material. The straps may be attached to the cast in a variety of suitable ways that will be apparent to those skilled in the art. The means of attachment will depend to some extent on the particular cast and techniques used for casting as well as the material of the straps. So long as the cast protector is securely attached, it will be adequate. Since casts are usually removed with a cast cutter, the means of attachment should take into consideration any interference with removal that the attachment may cause. For example, the metal strap may be screwed to the cast, both metal and fabric straps my attached with wrapping of casting material, duct taping it to the cast, wrapped to the cast with Elastikon™ elastic medical tape and like means.

In one embodiment the straps may be made of half of a hook and loop attachment material (such as Velcro™) or have the half of hook and loop strap attached to the inside surface of a strap. The leg cast can then be overwrapped with the other half of the hook and loop attachment material and the strap attached by connecting the two halves together— for example solid member strap hooks to leg wrap loops. Such a connection means using hook and loop straps can be used even without the leg cast to fit the solid member to the leg of an animal. While this invention generally deals with cast equine leg cast protection, it can suitable be used on other animals. For example, an elephant and rhino leg-to-foot is fairly straight making it difficult to fit a boot or shoe to the foot. The leg wrap can also be made of elastic material with strips of hook and loop to connect with the solid member. This allows the wrap to be more securely wrapped around the leg and still allow hook and loop attachment. The embodiment of the invention with connection means using hook and loop straps as above described could be used effectively to attach a solid member to an elephant or rhino foot.

The metal straps of an embodiment of the invention may be of various thicknesses or composition with the criteria that they be sufficiently malleable to allow them to be formed around the leg cast. Malleability allows the strips to be anchored to the cast in a manner that will hold them securely in place during use. Thin strips of stainless steel or aluminum are very suitable. Relatively thin stainless has very satisfactory strength and will not rust or corrode from the casting materials. Aluminum is somewhat softer, more easily molded but generally more expensive. It is preferred that the metal straps be perforated. As shown in the Figures, straps with elongate slots about two (2) inches long and ¼ inch wide in a 1¾ width strap work very well and are illustrative of some embodiments of the invention. In this strap about forty (40) % to fifty (50) % of the strap is cut away.

Instead of metal straps, fabrics or other flexible materials may also be used to attach the cast protector to the bottom of the leg cast as shown in FIG. 8. Four straps 302, 304, 306 and 308 are shown. In one aspect the fabric will be of the same material as the cast wrapping. It is generally preferred, however, to use stronger fabrics such as nylon ballistic cloth or ultra-highmolecular-weight polyethylene fabrics (Dyneema™ or Spectra™). In general, it is preferred that the cloth or fabric straps be longer than the metal straps. Lengths extending from the sides of the solid whole member top surface will be about 3 to 14 inches and preferably about 4 to 10 inches.

The width of the straps, both metal and fabric, will depend on the size of the solid whole member, the number of straps and the material used. In general solid whole members will be of approximately 3 to 8 inches in diameter and generally round (but may be slightly oblong with the length longer than the width—e.g. 6 inches long and 5.5 inches wide). As illustrative of suitable strap widths, a 3 inch diameter solid member will have straps of ¾ to 2 inches width or 8 to 21% of the solid member circumference length (¾"/3×3.14=8% of circumference length; ⅔×3.14=21% of circumference length). An 8 inch diameter solid whole member will have strap widths of about ¾ inch to 3 inches (3-12% of the length of the circumference of the solid member). A 6 inch diameter solid member will have strap widths of about ¾ inch to 3 inches—4 to 16% of the solid member circumference length. Thus, strap widths of about 3 to 16% of circumference length are suitable. The width is important to allow the straps to be molded around an equine leg cast. It is also important that there be open spaces between the straps at the interface with the solid whole member top surface. Wider straps may be split to facilitate wrapping.

Nylon ballistic cloth is generally very tough and durable fabric made with a "ballistic weave" or "seat belt" weave, typically a 2×2 or 2×3 basket weave. It can be woven from nylon yarns of various denier such as 840 denier and 1680 denier. Other particularly suitable fabrics include Dyneema™ and Spectra™. Dyneema and Spectra™ are Ultra-high-molecular-weight polyethylene fabrics that are gel spun through a spinneret to form oriented-strand synthetic fibers with yield strengths as high as 2.4 GPa (350,000 psi) and specific gravity as low as 0.97 (for Dyneema™ SK75). The straps and sheet made with these weaves from Dynema™ are very soft and smooth and provide easily formable straps.

The solid whole member is intended to be designed and sized to provide the optimum break-over for most applications; however, when constructed of a molded elastomer it may also be customized on site of use to an individual equine or individual need with standard farrier tools such as a rasp and knives. Molded elastomer enables an attending practitioner to further customize the device for each patient after looking at radiographs or other imaging means to the position of the coffin bone relative to the ground level and watch the horse's movement with the device. The solid member is preferably made of molded elastomeric polymer. It needs to be relatively hard and rigid, but not completely so. Molded polyurethane is very suitable and convenient to work with. It is preferred that thermoplastic polyurethane of about 45 to Shore A hardness be used, with Shore A hardness of 75 to 85 being especially suitable. In some applications, softer materials—Shore A f about 50 to 55 are preferred to provide additional cushioning of the hoof. The important point is that the hardness can be easily chosen and/or adapted to the individual need of the horse to which it is applied. Polyurethanes are easily moldable in open molds or by injection molding. Other polymer materials with similar characteristics as polyurethane, such as polyvinyl chlorides, styrene butadiene styrene polymer, epoxies and the like, are also usable. Choice of these will be well within the ability of those skilled in the polymer art to select.

Figure 12:
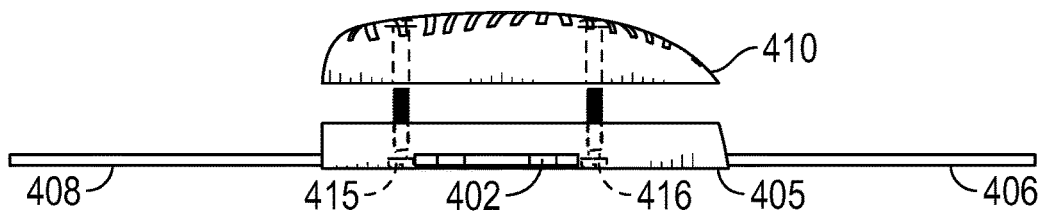
FIG. 12 is a side view of a two piece solid member embodiment of the invention.

In another embodiment the solid member is made in two pieces—one more rigid section with the straps attached and a rocker attachment attached to the more rigid solid base. This embodiment is illustrated in FIG. 12 where part 405 is the rigid whole solid member and 410 the attachable rocker bottom. Straps 402, 406 and 408 are shown. As shown, the bottom, 410, is attached to the solid whole member base 405, by barrel screws (415 and 416), but it may also be attached in other ways as by adhesives, horse shoe nails, direct bonding and the like. A suitable solid member base in a two piece arrangement will be polyurethane of a Shore A hardness of 90 plus.

The solid member, if made of polymer, may be reduced in weight by adding lower density small particles into the polymer as is done with polymer equine boot orthotics in U.S. patent application Ser. No. 13/396,191, filed Feb. 14, 2012, and U.S. patent Ser. No. 14/046,430 filed Oct. 4, 2013, the disclosures of which is incorporated herein by reference. The particles may be any material with sufficient durability for incorporation into a shock absorbing orthotic pad. In a preferred embodiment wherein the polymer of the solid member is polyurethane, the particles materials are of lower density than elastomeric polyurethane, capable of being adhered to by elastomeric polymer materials (preferably polyurethane), and generally, but optionally, spherical or elliptical in shape. Suitable materials may include, but are not limited to, polymers and elastomers, and preferably expanded foam or cellular formulation of these polymers. Specific examples include polypropylene and expanded polypropylene (PP), polyethylene and expanded polyethylene (PE), high density polyethylene (HDPE), ethylene propylene diene monomer (EPDM), polystyrene (PS), polyurethane and polyurethane foams, polystyrene, polybutadiene, styrene-butadiene rubber (SBR), and polyvinylchloride. In one embodiment, polypropylene and polyethylene are preferred, with closed-cell expanded polypropylene being particularly preferred for its low density, high durability, flexibility, resilience, and thermal insulation.

The particle cross section or diameters are desirably in the range of one (1) to six (6) millimeters (mm) ($3.9 \times 10^{-2}$ to $2.4 \times 10^{-1}$ inches). In a preferred embodiment, the particles have a diameter of approximately two (2) to four (4) mm ($7.9 \times 10^{-2}$ to $1.6 \times 10^{-1}$ inches), with approximately three (3) mm ($7.9 \times 10^{-2}$ inches) being particularly preferred. Particles of these sizes are small enough to be incorporated into the elastomer and large enough to not unduly increase viscosity of the polymer mixture during molding. If the particles are too large the result is a kind of permanent set reducing the flexibility and compressibility of the molded piece.

One of the key properties of the particles is their low density compared to the polymer of the solid member, resulting in a lower overall weight-to-volume ratio of the member. The difference in density between the particles and the polymer causes the particles to rise towards the top of the mold during casting, which becomes the bottom of the member. Because the particles are lower density than the polymer, they rise and accumulate at the top of the mold, which is the bottom of the pad, during molding. The member will then consist of a top layer comprised predominately of elastomer(s) that will be in contact with the hoof and a bottom layer of particle-filled polymer that provides a thermal barrier to protect the bottom of the cast, on which the device is fitted, from overheating. It is obvious that in other embodiments, the relative densities of the particles and elastomer(s) may be varied to control the relative positions of elastomer and particles.

The density of the particles is desirably in the range of about twenty (20) to five hundred twenty (520) grams/liter (g/l). For example, expanded polypropylene beads have a density range of about ten to two hundred (10-200) g/l, and preferred mid density beads have a density range of from about forty to one hundred twenty (40-120) g/l. Suitable polyurethane elastomers have densities of about one thousand twenty-five to one thousand seventy (1025-1070) g/l, so the ratio of density of elastomer to particle will be in the range of from about eight to twenty-eight (8-28). It is preferred that the particles be at least half the density of the elastomer and preferably no more than about 30% as dense.

In broad aspect, the method for manufacturing the lighter solid members comprises mixing particles with one or more elastomer component during curing to form a molded piece. In general, the basic process is to mix the elastomer components and catalysts, and to disperse the particles in unset polymer during curing while the polymer is still substantially in the liquid state. A mold of the desired size and shape is filled with the resulting mixture and the mixture is allowed to set and cure.

In a preferred embodiment, the method comprises mixing the chosen material with small particles before curing of the polymer is complete to form a homogeneous suspension. This mixture is poured into an open mold in which the open top of the mold is the top of the solid member. The particles will tend to rise to the top of the mold, accumulating in the upper portion of the molded piece. Once the elastomer is properly cured, the piece is removed from the mold. The resulting molded piece is comprised of a layer of elastomer in the upper portion of the member and a layer of elastomer-bound particles in the lower portion of the pad suitable for thermally insulating the hoof from the ground, absorbing shock, and reducing the overall weight of the member. A middle layer is comprised of an increasing concentration of particles dispersed in elastomer as one progresses from the top of the pad towards the bottom.

Casting the equine leg is conventional and well known by those, such as veterinarians, skilled in the art. The use of the attachment of this invention is not dependent on the particular kind of cast or casting material; however, in general, the use of the protective device will allow use of less casting material, reducing the weight of the cast. It is customary to use fiberglass casting materials that are well suited for use with the protective attachment of this invention. For example, an often used method of leg casting will include first placing a fabric stocking on the leg such as a 3M™ Synthetic Cast Stockinet (a synthetic stockinet underlayment for all standard casting applications, and suitable for use with all casting materials, plaster and synthetic). This stocking may be then overlaid with casting tape such as 3M™ Vetcast™ Plus Veterinary Casting Tape 1468-4.

As the casting tape is applied, the straps of the protective device of this invention may be taped into the cast structure. Alternatively, the straps may be attached by adhesive, by screwing the straps to the finished, use of hook and loop straps and leg cast wrap and other such means as will be obvious to those skilled in the art.

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense and the scope of the invention should be limited only by the appended claims.

The invention claimed is:

1. An equine leg cast attachment comprising a solid whole member suitable for attachment underneath an equine leg cast which stabilizes a portion of a body of an equine, wherein the solid whole member:
    (a) is configured to be capable of being disposed beneath an equine hoof and to substantially cover an entire underside of an equine hoof;
    (b) comprises a top face, a bottom face and having a circumference with a length around, and
    (c) further comprises malleable attachment straps attached to the solid whole member and extending, in a generally even spacing around the circumference from at least three sides of the solid whole member, wherein the malleable attachment straps are configured to be capable of securing the solid whole member both to the equine leg cast and underneath the equine hoof, the malleable attachment straps being so configured at least by: (i) being configured with dimensions and of material capable of being bent or folded upward, in a plane perpendicular to the top face of the solid whole member and generally parallel to a leg of the equine upon attachment to the equine leg cast, and (ii) being of widths between about three (3) to sixteen (16) percent of the length of the circumference of the solid whole member.

2. The equine leg cast attachment of claim 1 wherein the malleable attachment straps are malleable metal.

3. The equine leg cast attachment of claim 2 wherein the malleable attachment straps are perforated.

4. The equine leg cast attachment of claim 1 wherein the malleable attachment straps are fabric.

5. The equine leg cast attachment device of claim 4 wherein the malleable attachment straps comprise one half of a hook and loop strip or sheet, having a hook or loop side, with the hook or loop side facing inward relative to the solid whole member.

6. The equine leg cast attachment of claim 1 wherein the top face of the solid whole member is tapered.

7. The equine leg cast attachment of claim 6 wherein the top face of the solid whole member is tapered towards the front, from a centerline of the solid whole member.

8. The equine leg cast attachment of claim 6 wherein the bottom face of the solid whole member is patterned on the bottom.

9. The equine leg cast attachment device of claim 1 wherein the solid whole member is made of a single material that is a polymer.

10. The equine leg cast attachment of claim 9 wherein the polymer is polyurethane.

11. The equine leg cast attachment of claim 1 wherein the solid whole member comprises two solid whole structures that are vertically attachable together.

12. The equine leg cast attachment of claim 1 wherein the malleable attachment straps extend from four sides of the solid whole member.

13. The equine leg cast attachment device of claim 1 wherein the solid whole member comprises at least one primary polymer, into which is incorporated particles of lower density than the primary polymer to reduce weight of the solid whole member.

14. An equine leg cast assembly comprising an equine leg cast: (i) encasing a leg of an equine and stabilizing a portion of a body of the equine, (ii) comprising veterinary casting material, and (iii) having a bottom, to which is attached an equine leg cast attachment comprising a horizontally whole solid member, which is thereby disposed beneath and substantially covering an entire underside of a hoof of the equine, the solid member: (a) having a top face, a bottom face and having a circumference with a length around and (b) having malleable attachment straps attached to the solid member and extending, in a generally even spacing around the circumference from at least three sides of the solid member, wherein the malleable attachment straps are configured to be capable of securing the solid member both to the equine leg cast and underneath the hoof, the malleable attachment straps being so configured at least by: (1) being configured with dimensions and of material capable of being bent or folded upward in a plane perpendicular to the top face of the solid member and generally parallel to the equine's leg upon attachment to the equine leg cast, and (2) being of widths between about three (3) to sixteen (16) percent of the length of the circumference of the solid member, the strap widths being measured at the side of the solid member.

15. The equine leg cast assembly of claim 14 wherein the malleable attachment straps are perforated metal.

16. The equine leg cast assembly of claim 14 wherein the solid member is made of polymer and is tapered towards the front, from a centerline, front to back, of the solid member.

17. The equine leg cast assembly of claim 14 wherein the bottom face of the solid member is patterned.

18. The equine leg cast assembly of claim 14 wherein the malleable attachment straps are attached to the equine leg cast by overwrapping with casting tape.

19. A method of protecting and providing improved mobility in an equine when in a leg cast which is on a leg of the equine and which stabilizes a portion of the equine's body, the method comprising fitting to a bottom of the leg cast, and underneath a hoof of the equine, an attachment device comprising a horizontally whole solid member, the solid member: (a) having a top face and a bottom face, (b) being configured to substantially cover an entire underside of the hoof, and (c) having malleable attachment straps attached to the solid member and extending, in a generally even spacing around the circumference from at least three sides of the solid member, which straps are configured with dimensions and of material capable of being bent or folded upward in a plane, perpendicular to the top face of the solid member and generally parallel to the leg, thereby being suitable to attach the solid member to the leg cast by attaching the straps to sides of the leg cast.

20. The method of claim 19 comprising: (1) fitting the attachment device on the bottom of the leg cast, the leg cast being a new cast on the leg, (2) folding the straps of the attachment device up alongside the leg on which at at least some protective material has been placed, and (3) applying casting tape over the folded up straps to secure them to the new cast by incorporating them into the new cast during construction thereof.

* * * * *